US006177271B1

(12) United States Patent
Butts et al.

(10) Patent No.: US 6,177,271 B1
(45) Date of Patent: Jan. 23, 2001

(54) AMBIENT TEMPERATURE STABILIZATION CONTROL SYSTEM FOR LABORATORY INCUBATOR

(75) Inventors: Charles G. Butts, Weaverville; Timothy R. Runion, Asheville, both of NC (US)

(73) Assignee: SPX Corporation, Muskegon, MI (US)

( * ) Notice: Under 35 U.S.C. 154(b), the term of this patent shall be extended for 0 days.

(21) Appl. No.: 09/294,271

(22) Filed: Apr. 19, 1999

(51) Int. Cl.[7] ...................................................... C12M 1/00
(52) U.S. Cl. .................................... 435/303.1; 435/303.2; 219/407; 236/2; 237/3; 600/22
(58) Field of Search ............................. 435/303.1, 303.2, 435/286.1; 219/407; 236/3; 237/3; 600/22

(56) References Cited

U.S. PATENT DOCUMENTS 5,281,516 * 1/1994 Stapleton et al. ........................ 435/3
5,783,439 * 7/1998 Reichler et al. .................. 435/286.1

* cited by examiner

*Primary Examiner*—David A. Redding
(74) *Attorney, Agent, or Firm*—Hovey Williams Timmons & Collins

(57) ABSTRACT

A laboratory incubator (10) having an improved temperature control assembly (14) that more effectively maintains the temperature within the incubator in a desired range and more accurately controls the rate of heat loss from the laboratory incubators as ambient temperatures rise. The incubator includes a housing (12) having an enclosed incubation chamber (18) therein; a heater (22) positioned within the housing for heating the chamber; a cooling device (24) positioned within the housing for cooling the walls of the housing; and a controller (26) for controlling the operation of the heater and the cooling device to maintain a temperature in the chamber within a set temperature range. The cooling device includes an electrically operated peltier device operable to both cool the chamber and to assist the heater in heating the chamber.

4 Claims, 1 Drawing Sheet

AMBIENT TEMPERATURE STABILIZATION CONTROL SYSTEM FOR LABORATORY INCUBATOR

BACKGROUND OF THE INVENTION

1. Field of the Invention

Figure 2:
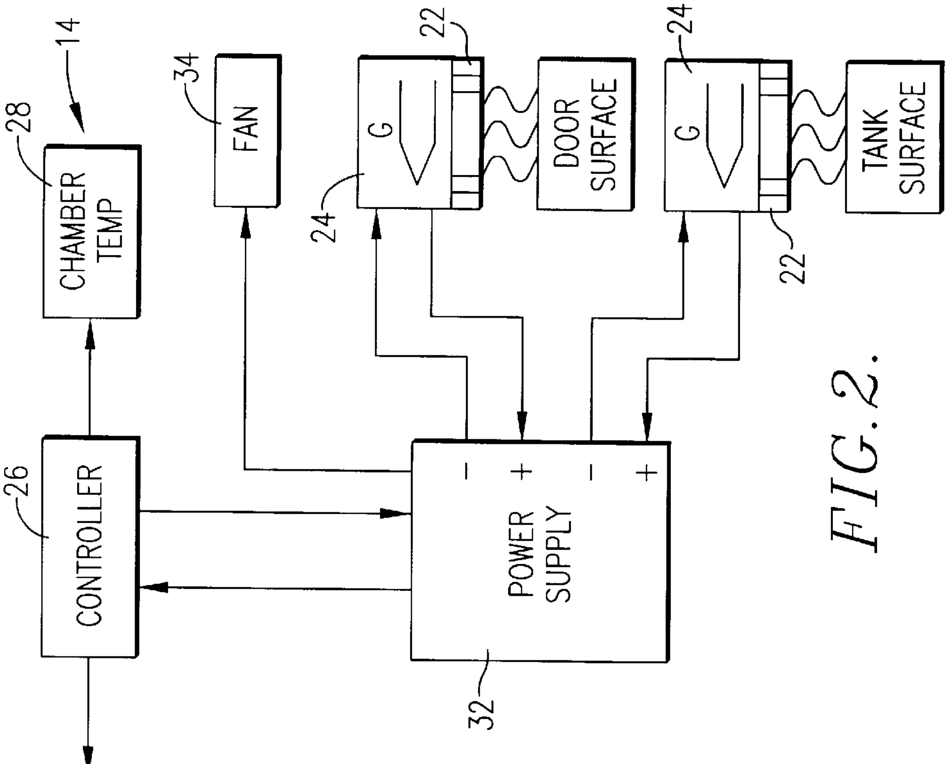

The present invention relates to laboratory incubators, and more particularly to a laboratory incubator having an improved temperature control assembly that more effectively maintains the temperature within the incubator in a desired range and that more accurately controls the rate of heat loss from the incubator as ambient temperatures rise.

2. Description of the Prior Art

The temperature within a laboratory incubator must be maintained within a certain operating temperature range that is typically above ambient temperatures. Therefore, it is common to provide laboratory incubators with heating devices that are periodically cycled to maintain the temperature within the interior of the incubators in this range. Heaters can effectively maintain the temperature within a desired range as long as the ambient temperature around the incubator is substantially lower then the desired operating range. However, when the ambient temperature increases so that it approaches the desired operating temperature of the incubator, the rate of heat loss through the walls of the incubator decreases so that excess heat from the chamber does not dissipate therefrom. Typically, if ambient temperatures rise to within 5° C. of the incubator's desired operating temperature, the internal temperature within the incubation chamber begins to rise at the same rate of change as the ambient temperature, causing the temperature within the incubator to rise above its desired operating range.

Prior art attempts to solve this problem include the placement of a jacket of cooling liquid or refrigerant around an incubator. When the ambient temperature rises to a certain high level, the liquid in the jacket is cooled by cooling coils to increase the incubator's heat loss so that the temperature within the incubator can be more easily maintained in a desired range. These prior art cooling devices are impractical and sometimes ineffective, however, because they are expensive, bulky, and difficult to control.

Therefore, there is a need for a laboratory incubator having an improved temperature control assembly for more accurately maintaining the operating temperature within the incubator in a desired operating range and for maintaining a minimum heat loss rate from the incubator as the ambient temperature around the incubator rises.

OBJECTS AND SUMMARY OF THE INVENTION

The present invention solves the above-described problems and provides a distinct advance in the art of laboratory incubators. More particularly, the present invention provides a laboratory incubator having an improved temperature control assembly that more effectively maintains the temperature within the incubator in a desired range and that more accurately controls the rate of heat loss from the incubator as ambient temperatures rise.

The incubator of the present invention broadly includes a housing having an enclosed incubation chamber therein; a heater positioned within the housing for heating the chamber; a cooling device positioned within the housing for cooling the chamber; and a controller for controlling the operation of the heater and the cooling device to maintain the temperature in the chamber within a desired temperature range. In accordance with one aspect of the invention, the cooling device is an electrically operated peltier device operable to both cool the chamber and to assist the heater in heating the chamber.

In operation, the controller cycles the heater whenever the ambient temperature is significantly lower than the desired operating temperature of the incubator to maintain the operating temperature of the incubator within a desired range. Then, if the ambient temperature approaches the operating temperature of the incubator, the controller cycles the peltier device to cool the walls of the incubator for increasing the rate of heat loss from the interior of the incubator to the walls. This allows excess heat within the incubator to dissipate through the walls of the incubator to prevent the incubator's temperature from rising above the desired operating range.

The peltier device is less expensive, easier to install, and easier to control than prior art cooling devices used in incubators. Moreover, the peltier device is also operable for heating the walls of the incubator for decreasing the heat loss from the chamber to assist the heater in maintaining the temperature within the incubator when the ambient temperature outside the incubator is significantly below the desired operating temperature within the incubator. Thus, unlike prior art cooling jackets, the peltier device can be controlled to either increase or decrease the heat loss through the walls of the incubator.

BRIEF DESCRIPTION OF THE DRAWING FIGURES

Figure 1:
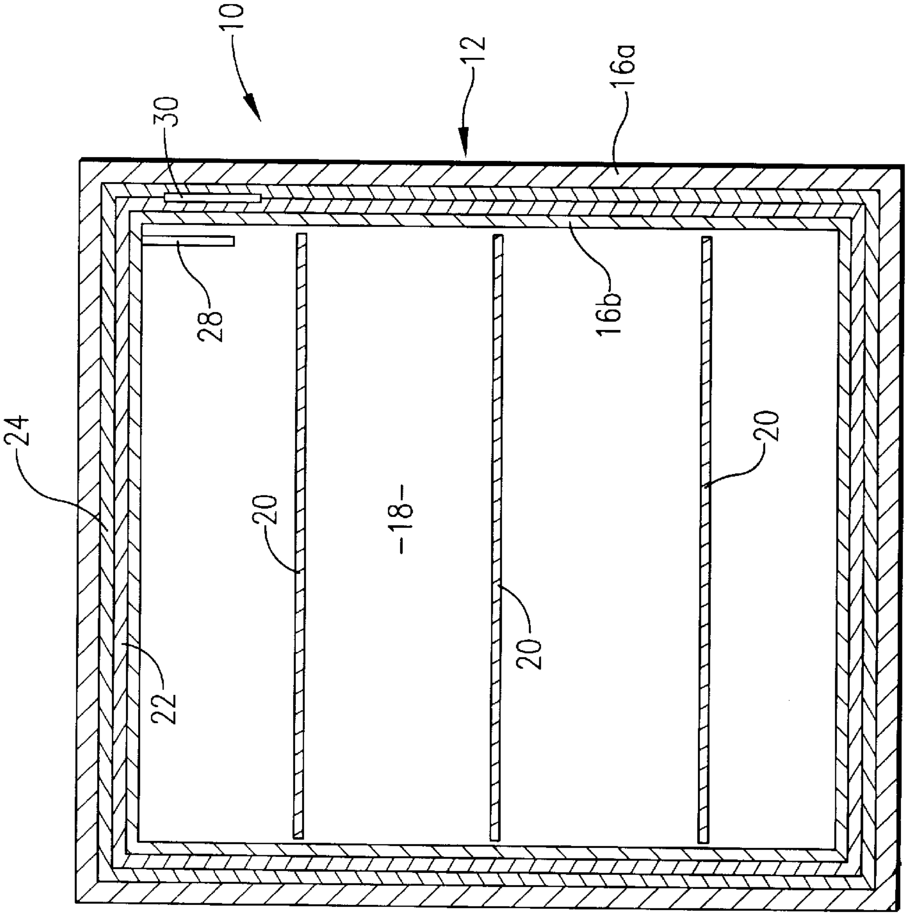

A preferred embodiment of the present invention is described in detail below with reference to the attached drawing figures, wherein:

FIG. 1 is a vertical sectional view of a laboratory incubator constructed in accordance with a preferred embodiment of the present invention; and FIG. 2 is a schematic diagram of the temperature control assembly of the incubator.

DETAILED DESCRIPTION OF THE PREFERRED EMBODIMENTS

Referring to the drawing figures, a laboratory incubator 10 constructed in accordance with a preferred embodiment of the invention is illustrated. The incubator broadly includes a housing 12 (FIG. 1) and a temperature control assembly broadly referred to by the numeral 14 (FIG. 2).

In more detail, the housing 12 includes spaced-apart outer and inner walls 16*a*, 16*b*, with the inner wall defining an enclosed incubation chamber 18 therein, a hinged door (not shown) for gaining access to the incubation chamber, and a plurality of stacked shelves 20 for placing specimens thereon. The housing may be constructed of any materials conventional to incubators and may be sized for any desired application.

The temperature control assembly 14 is operatively coupled with the housing 12 to control the temperature within chamber 18 so that the temperature remains within a desired range. For example, in one application, the control assembly maintains the temperature within the chamber at approximately 38° C. As best illustrated in FIG. 2, the temperature control assembly 14 includes a heater 22, a cooling device 24, a controller 26, a pair of temperature sensors 28,30, and a power supply 32.

The heater 22 is positioned between the outer and inner walls 16*a*, 16*b* of the housing 12 and is operable for heating the incubation chamber 18 when the ambient temperature around the incubator is below the incubator's desired operating temperature for maintaining the operating temperature of the chamber within the desired temperature range. The heater may be any conventional heating device, but preferably includes a rope-type heating element laminated between two layers of flexible aluminum foil material. One of the layers of foil material has a layer of adhesive thereon so that the heater can be adhered to the outside surface of the inner wall 16*b* as illustrated in FIG. 1. As illustrated in FIG. 2, the heater is also preferably applied to the interior of the housing door. One preferred embodiment of the heater is manufactured by Springfield Wire of Springfield, Mass.

In accordance with one aspect of the present invention, the cooling device 24 is a peltier-type device that provides either a coiling or heating effect depending on the direction of current passing therethrough. The peltier device includes a junction of two dissimilar metals such as p-type semiconductor pellets and n-type semi-conductor pellets that are sandwiched between two layers of ceramic substrate. A layer of adhesive is placed on one of the substrate layers so that the peltier device may be adhered to the inside surface of the outer wall 16a as illustrated in FIG. 1. As illustrated in FIG. 2, the cooling device is also preferably applied to the interior of the housing door. A fan 34 may also be provided within the incubation chamber 18 for circulating air therein.

As illustrated in FIG. 2, the power supply 32 delivers power to the cooling device 24, heater 22, and fan 34. Operation of the power supply is in turn controlled by the controller as described below. The controller may be any conventional programmable microprocessor device.

As illustrated in FIG. 1, temperature sensors 28,30 are mounted within the housing 12 for monitoring the temperature within the incubation chamber 18 and the temperature between the walls 16*a,* 16*b* of the housing. More specifically, the temperature sensor 28 is preferably positioned inside the inner wall 16*b* of the housing so that it monitors the air temperature within the incubation chamber. The other temperature sensor 30 is preferably sandwiched between the heater 22 and the peltier cooling device 24 so that it monitors the temperature between the walls of the housing. As illustrated in FIG. 2, both temperature sensors are coupled with the controller 26 for delivering signals representative of their sensed temperature thereto.

In operation, the temperature control assembly 14 functions in two modes to maintain the temperature within the incubation chamber 18: a heating mode to increase the air temperature within the chamber, and a cooling mode to increase the heat loss from the chamber. Specifically, whenever the ambient temperature around the housing is lower than the desired operating temperature of the incubator, the controller 26 directs the power supply 32 to cycle the heater 22 to maintain the operating temperature of the incubator within a desired range. The controller may also operate the peltier cooling device 24 in its heating mode for heating the walls of the incubator for decreasing the heat loss from the chamber. This assists the heater in maintaining the temperature within the incubator when the ambient temperature outside the incubator is significantly below the operating temperature within the incubator.

When the ambient temperature around the housing rises so that it approaches the operating temperature of the incubator, the controller 26 cycles the peltier cooling device 24 in its cooling mode to cool the walls of the incubator for increasing the rate of heat loss from the interior of the incubator through the walls 16*a,* 16*b.* This allows the heat with the incubator to dissipate through the walls of the incubator to prevent the temperature from within the incubator from rising above the desired operating range.

Although the invention has been described with reference to the preferred embodiment illustrated in the attached drawing figures, it is noted that equivalents may be employed and substitutions made herein without departing from the scope of the invention as recited in the claims.

Having thus described the preferred embodiment of the invention, what is claimed as new and desired to be protected by letters patent includes the following:

1. A lab incubator comprising:

a housing having an outer housing wall and an inner chamber wall defining an enclosed incubation chamber therein; and a temperature control assembly including a heater positioned within the housing adjacent the inner chamber wall for heating the chamber, a cooling device positioned within the housing adjacent the outer housing wall and in contact with the heater for cooling the walls of the housing, and a controller for controlling the operation of the heater and the cooling device to maintain a temperature in the chamber within a desired temperature range.

2. The lab incubator as set forth in claim 1, the heater including a heating element laminated between two layers of aluminum foil material and a layer of adhesive on one side of one of the layers of aluminum foil material for adhering the heater to an interior wall of the incubation chamber.

3. The lab incubator as set forth in claim 1, further including a temperature sensor coupled with the controller for monitoring the temperature in the chamber for use by the controller in controlling the operation of the heater and the cooling device.

4. The lab incubator as set forth in claim 3, further including a second temperature sensor coupled with the controller for monitoring the temperature in the chamber.

* * * * *